(12) United States Patent
Bange et al.

(10) Patent No.: US 7,904,169 B2
(45) Date of Patent: Mar. 8, 2011

(54) IMPLANTABLE MEDICAL DEVICE TELEMETRY WITH PERIODIC FREQUENCY HOPPING

(75) Inventors: Joseph E. Bange, Eagan, MN (US); Vineel Vallapureddy, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/579,092

(22) Filed: Oct. 14, 2009

(65) Prior Publication Data

US 2010/0036463 A1    Feb. 11, 2010

Related U.S. Application Data

(62) Division of application No. 11/456,942, filed on Jul. 12, 2006, now Pat. No. 7,623,922.

(51) Int. Cl.
*A61N 1/00* (2006.01)

(52) U.S. Cl. ............... 607/60; 340/539.12; 128/903

(58) Field of Classification Search .............. 607/60
See application file for complete search history.

(56) References Cited

U.S. PATENT DOCUMENTS

| | | | |
|---|---|---|---|
| 4,633,411 A | 12/1986 | Bliss | |
| 4,799,059 A | 1/1989 | Grindahl et al. | |
| 5,287,384 A | 2/1994 | Avery et al. | |
| 5,342,408 A | 8/1994 | deCoriolis et al. | |
| 5,394,433 A | 2/1995 | Bantz et al. | |
| 5,562,713 A | 10/1996 | Silvian | |
| 5,568,510 A | 10/1996 | Tam | |
| 5,603,088 A | 2/1997 | Gorday et al. | |
| 5,612,960 A | 3/1997 | Stevens et al. | |
| 5,617,871 A | 4/1997 | Burrows | |
| 5,683,432 A | 11/1997 | Goedeke et al. | |
| 5,729,680 A | 3/1998 | Belanger et al. | |
| 5,752,977 A | 5/1998 | Grevious et al. | |
| 5,843,139 A | 12/1998 | Goedeke et al. | |
| 5,870,391 A | 2/1999 | Nago | |
| 5,887,022 A | 3/1999 | Lee | |
| 5,940,384 A | 8/1999 | Carney et al. | |
| 6,031,863 A | 2/2000 | Jusa et al. | |
| 6,088,381 A | 7/2000 | Myers, Jr. | |
| 6,130,905 A | 10/2000 | Wakayama | |

(Continued)

FOREIGN PATENT DOCUMENTS

EP     1308184 A2     5/2003

(Continued)

OTHER PUBLICATIONS

"U.S. Appl. No. 11/456,937, Non-Final Office Action mailed Jul. 31, 2008", 13 pgs.

(Continued)

*Primary Examiner* — Carl H Layno
*Assistant Examiner* — Gary A Porter, Jr.
(74) *Attorney, Agent, or Firm* — Schwegman, Lundberg & Woessner, P.A.

(57) ABSTRACT

A far-field radio-frequency (RF) telemetry system for data transmission between an implantable medical device and an external system includes a plurality of channels each representing a frequency band within a predetermined frequency range. The data transmission is performed using at least one active channel at any instant. Channel hopping is performed on a periodic basis throughout a telemetry session such that the active channel keeps scanning through an array of channels selected from the plurality of channels. If a data frame is not successfully transmitted, it is repeatedly re-transmitted using the current and/or the next active channels until its transmission becomes successful.

14 Claims, 7 Drawing Sheets

U.S. PATENT DOCUMENTS

| | | |
|---|---|---|
| 6,219,580 B1 | 4/2001 | Faltys et al. |
| 6,223,083 B1 | 4/2001 | Rosar |
| 6,243,568 B1 | 6/2001 | Detlef et al. |
| 6,381,492 B1 | 4/2002 | Rockwell et al. |
| 6,424,867 B1 | 7/2002 | Snell et al. |
| 6,434,429 B1 | 8/2002 | Kraus et al. |
| 6,443,891 B1 | 9/2002 | Grevious |
| 6,471,645 B1 | 10/2002 | Warkentin et al. |
| 6,490,487 B1 | 12/2002 | Kraus et al. |
| 6,535,763 B1 | 3/2003 | Hiebert et al. |
| 6,535,766 B1 | 3/2003 | Thompson et al. |
| 6,600,952 B1 | 7/2003 | Snell et al. |
| 6,631,296 B1 | 10/2003 | Parramon et al. |
| 6,704,346 B1 | 3/2004 | Mansfield |
| 6,763,269 B2 | 7/2004 | Cox |
| 6,801,807 B2 | 10/2004 | Abrahamson |
| 6,868,288 B2 | 3/2005 | Thompson |
| 6,897,788 B2 | 5/2005 | Khair et al. |
| 6,978,181 B1 | 12/2005 | Snell |
| 6,985,773 B2 | 1/2006 | Von Arx et al. |
| 7,013,178 B2 | 3/2006 | Reinke et al. |
| 7,146,134 B2 | 12/2006 | Moon et al. |
| 7,177,700 B1 | 2/2007 | Cox |
| 7,218,969 B2 | 5/2007 | Vallapureddy et al. |
| 7,280,872 B1 | 10/2007 | Mosesov et al. |
| 7,289,853 B1 | 10/2007 | Campbell et al. |
| 7,573,422 B2 | 8/2009 | Harvey et al. |
| 7,623,922 B2 | 11/2009 | Bange et al. |
| 7,787,953 B2 | 8/2010 | Vallapureddy et al. |
| 7,801,620 B2 | 9/2010 | Freeberg |
| 2001/0012955 A1 | 8/2001 | Goedeke et al. |
| 2002/0039380 A1 | 4/2002 | Steed et al. |
| 2002/0109621 A1 | 8/2002 | Khair et al. |
| 2002/0123672 A1 | 9/2002 | Christophersom et al. |
| 2002/0143372 A1 | 10/2002 | Snell et al. |
| 2002/0183806 A1 | 12/2002 | Abrahamson et al. |
| 2003/0026223 A1 | 2/2003 | Eriksson et al. |
| 2003/0050535 A1 | 3/2003 | Bowman, IV et al. |
| 2003/0097157 A1 | 5/2003 | Wohlgemuth et al. |
| 2003/0114891 A1 | 6/2003 | Hiebert et al. |
| 2003/0146835 A1 | 8/2003 | Carter |
| 2003/0149459 A1 | 8/2003 | Von Arx et al. |
| 2003/0187484 A1 | 10/2003 | Davis et al. |
| 2003/0220673 A1 | 11/2003 | Snell |
| 2004/0047434 A1 | 3/2004 | Waltho |
| 2004/0127959 A1 | 7/2004 | Amundson et al. |
| 2004/0167587 A1 | 8/2004 | Thompson |
| 2004/0176811 A1 | 9/2004 | Von Arx et al. |
| 2004/0176822 A1 | 9/2004 | Thompson et al. |
| 2005/0222933 A1 | 10/2005 | Wesby |
| 2005/0245992 A1 | 11/2005 | Persen et al. |
| 2006/0030901 A1 | 2/2006 | Quiles et al. |
| 2006/0030903 A1 | 2/2006 | Seeberger et al. |
| 2006/0071756 A1 | 4/2006 | Steeves |
| 2006/0161222 A1 | 7/2006 | Haubrich et al. |
| 2006/0161223 A1 | 7/2006 | Vallapureddy et al. |
| 2006/0195161 A1 | 8/2006 | Li |
| 2006/0195162 A1 | 8/2006 | Arx et al. |
| 2007/0049983 A1 | 3/2007 | Freeberg |
| 2007/0185550 A1 | 8/2007 | Vallapureddy et al. |
| 2007/0260293 A1 | 11/2007 | Carpenter et al. |
| 2008/0015655 A1 | 1/2008 | Bange et al. |
| 2008/0015656 A1 | 1/2008 | Bange et al. |
| 2008/0228237 A1 | 9/2008 | Bange et al. |
| 2010/0168819 A1 | 7/2010 | Freeberg |

FOREIGN PATENT DOCUMENTS

| | | |
|---|---|---|
| EP | 1308184 A3 | 5/2004 |
| EP | 1495783 A1 | 1/2005 |
| WO | WO-9819400 A1 | 5/1998 |
| WO | WO-9912302 A1 | 3/1999 |
| WO | WO-2008008564 A2 | 1/2008 |
| WO | WO-2008008564 A3 | 1/2008 |
| WO | WO-2008008565 A2 | 1/2008 |
| WO | WO-2008008565 A3 | 1/2008 |
| WO | WO-2008027655 A1 | 3/2008 |
| WO | WO-2008/112222 A3 | 9/2008 |
| WO | WO-2008112222 A2 | 9/2008 |

OTHER PUBLICATIONS

"U.S. Appl. No. 11/456,937, Response filed Oct. 15, 2008 to Non Final Office Action mailed Jul. 31, 2008", 10 pgs.

"U.S. Appl. No. 11/456,937, Response filed Feb. 23, 2009 to Final Office Action mailed Dec. 22, 2008", 9 pgs.

"U.S. Appl. No. 11/456,937, Non-Final Office Action mailed Jul. 7, 2009", 11 pgs.

"U.S. Appl. No. 11/456,937, Response filed Oct. 7, 2009 to Non Final Office Action mailed Jul. 7, 2009", 13 pgs.

"U.S. Appl. No. 11/456,942, Non-Final Office Action mailed Aug. 18, 2008", 15 pgs.

"U.S. Appl. No. 11/456,942, Response filed Nov. 18, 2008 to Non Final Office Action mailed Aug. 18, 2008", 10 pgs.

"U.S. Appl. No. 11/456,942, Final Office Action mailed Mar. 10, 2009", 15 pgs.

"U.S. Appl. No. 11/456,942, Response filed May 4, 2009 to Final Office Action mailed Mar. 10, 2009", 9 pgs.

"U.S. Appl. No. 11/469,804, Non-Final Office Action mailed Sep. 18, 2009", 7 pgs.

"U.S. Appl. No. 11/456,937, Final Office Action Mailed Dec. 22, 2008", 10 pgs.

"International Application Serial No. PCT/US2007/003216, International Search Report mailed Sep. 12, 2008", 4 pgs.

"International Application Serial No. PCT/US2008/003216, Written Opinion mailed Sep. 12, 2008", 8 pgs.

"PCT Application No. PCT/US2007/069424, International Search Report mailed Dec. 27, 2007", 4 pgs.

"PCT Application No. PCT/US2007/069424, Written Opinion mailed Dec. 27, 2007", 9 pgs.

"PCT Application No. PCT/US2007/069426, International Search Report mailed Dec. 27, 2007", 4 pgs.

"PCT Application No. PCT/US2007/069426, Written Opinion mailed Dec. 27, 2007", 8 pgs.

"PCT Application No. PCT/US2007/072827, International Search Report mailed Dec. 10, 2007", 4 pgs.

"PCT Application No. PCT/US2007/072827, Written Opinion mailed Dec. 10, 2007", 6 pgs.

Adams, J. T, "An introduction IEEE STD 802.15.4", *Aerospace conference*, 2006 IEEE big sky, (Mar. 4-11, 2006), 1-8.

Duflot, M., et al., "A formal analysis of bluetooth device discovery", *International journal on software tools for technology transfer*, 8 (6), (Jul. 5, 2006), 621-632.

Golmie, N., et al., "The Evolution of Wireless LANs and PANs -Bluetooth and WLAN coexistance: challenges and solutions", *IEEE Personal Communications*, 10(6), (Dec. 2003), 22-29.

Zhu, H., et al., "A survey of quality of service in IEEE 802.11 Networks", *IEEE Wireless Communications, IEEE Service Center*, Piscataway, NJ, US, 11(4), (Aug. 2004), 6-14 pgs.

"U.S. Appl. No. 11/214,508, Notice of Allowance mailed May 18, 2010", 4 pgs.

"U.S. Appl. No. 11/214,508, Notice of Allowance mailed Nov. 18, 2009", 4 pgs.

"U.S. Appl. No. 11/456,937, Examiner Interview Summary mailed Jun. 2, 2010", 3 pgs.

"U.S. Appl. No. 11/456,937, Non-Final Office Action mailed Mar. 12, 2010", 9 pgs.

"U.S. Appl. No. 11/456,937, Response filed Jun. 14, 2010 to Non Final Office Action mailed Mar. 12, 2010", 11 pgs.

"U.S. Appl. No. 11/685,577, Non-Final Office Action mailed Mar. 29, 2010", 12 pgs.

"U.S. Appl. No. 11/685,577, Response filed Jul. 29, 2010 to Non-Final Office Action mailed Mar. 29, 2010", 14 pgs.

"U.S. Appl. No. 11/733,339, Interview Summary mailed Aug. 13, 2009", 2 pgs.

"U.S. Appl. No. 11/733,339, Notice of Allowance mailed Feb. 25, 2010", 6 pgs.

"U.S. Appl. No. 11/733,339, Notice of Allowance mailed Apr. 21, 2010", 6 pgs.

"U.S. Appl. No. 11/733,339, Response filed Dec. 4, 2009 to Non-Final Office Action mailed Sep. 9, 2009", 11 pgs.

"Australian Application Serial No. 2008226849, Examiner Report mailed Jun. 15, 2010", 2 pgs.

"European Application Serial No. 07811917.9, Response filed Apr. 22, 2010 to Office Action mailed Oct. 28, 2009", 18 pgs.

"European Application Serial No. 07811917.9, Office Action Mailed Oct. 28, 2009", 4 pgs.

"European Application Serial No. 08726709.2, Office Action mailed Jul. 23, 2010", 6 pgs.

IMPLANTABLE MEDICAL DEVICE TELEMETRY WITH PERIODIC FREQUENCY HOPPING

CLAIM OF PRIORITY

This application is a Divisional of U.S. application Ser. No. 11/456,942, filed Jul. 12, 2006, which is incorporated herein by reference in its entirety.

CROSS-REFERENCE TO RELATED APPLICATION

This application is related to, commonly assigned, U.S. patent application Ser. No. 11/039,200, entitled "DYNAMIC CHANNEL SELECTION FOR RF TELEMETRY WITH IMPLANTABLE DEVICE," filed on Jan. 19, 2005, now U.S. Pat. No. 7,218,969, and U.S. patent application Ser. No. 11/456,937, entitled "IMPLANTABLE MEDICAL DEVICE TELEMETRY WITH ADAPTIVE FREQUENCY HOPPING," filed on Jul. 12, 2006, now U.S. Pat. No. 7,623,922, which are hereby incorporated by reference in their entirety.

TECHNICAL FIELD

This document relates generally to telemetry for implantable medical systems and particularly to a frequency agile telemetry system with periodic frequency hopping.

BACKGROUND

Medical devices are implanted in human bodies for monitoring physiological conditions, diagnosing diseases, treating diseases, or restoring functions of organs or tissues. Examples of such implantable medical devices include cardiac rhythm management (CRM) devices, neural stimulators, neuromuscular stimulators, drug delivery devices, and biological therapy devices. When an implantable medical device is intended for long-term use in a patient, its size and power consumption are limited by implantability and longevity requirements. Consequently, many implantable medical devices depend on external systems to perform certain functions. Communication between an implantable medical device and an external system is performed via telemetry. Examples of specific telemetry functions include programming the implantable medical device to perform certain monitoring or therapeutic tasks, extracting an operational status of the implantable medical device, transmitting real-time physiological data acquired by the implantable medical device, and extracting physiological data acquired by and stored in the implantable medical device.

One type of telemetry between the implantable medical device and the external system is based on inductive coupling between two closely-placed coils using the mutual inductance between these coils. One of the coils is part of the implantable medical device, and the other coil is part of the external system and is typically attached to the patient during a telemetry session. This type of telemetry is referred to as inductive telemetry or near-field telemetry because the coils must be closely situated for obtaining magnetically coupled communication.

Far-field radio-frequency (RF) telemetry provides another means for communication between the implantable medical device and the external system. The far-field RF telemetry is performed using an RF transceiver in the implantable medical device and an RF transceiver in the external system. The far-field RF telemetry frees the patient from any body surface attachment that limits mobility.

The far-field RF telemetry between the implantable medical device and the external system often operates in an environment where various sources of electromagnetic interference exist. For example, a far-filed RF telemetry link operating at a frequency within an unlicensed frequency band may be subjected to environmental interferences from various medical electronic devices, communication devices, and home electronic appliances. Such interferences may interrupt data transmission through the far-filed RF telemetry link.

Therefore, there is a need to ensure efficiency by minimizing interruption of far-field RF telemetry between an external system and an implanted device when interferences are present.

SUMMARY

A far-field RF telemetry system for data transmission between an implantable medical device and an external system includes a plurality of channels each representing a frequency band within a predetermined frequency range. The data transmission is performed using at least one active channel at any instant. Channel hopping is performed on a periodic basis throughout a telemetry session such that the active channel keeps scanning through an array of channels selected from the plurality of channels. If a data frame is not successfully transmitted, it is repeatedly re-transmitted using the current and/or the next active channels until its transmission becomes successful.

In one embodiment, a CRM system includes an implantable medical device and an external system communicating with each other via telemetry. The implantable medical device includes a CRM module and an implant telemetry module. The external system includes a programming module and an external telemetry module. The implant telemetry module and the external telemetry module each include a telemetry circuit that includes an antenna, a transceiver, and a telemetry controller. The transceiver includes a plurality of channels each representing a predetermined frequency band for data transmission between the implantable medical device and the external system. The telemetry controller controls data transmission and channel hopping during synchronous and asynchronous scan modes. The channel hopping includes selecting an active channel from the plurality of channels on an approximately periodic basis. The data transmission is performed using the active channel during a synchronous scan mode during which the channel hopping in the external system and the channel hopping in the implantable medical device are synchronous. The telemetry controller starts an asynchronous scan mode after the channel hopping in the external system and the channel hopping in the implantable medical device become asynchronous. During the asynchronous scan mode, the telemetry controller restores the synchronization of the channel hopping in the external system and the channel hopping in the implantable medical device.

In one embodiment, a method for data transmission between an implantable medical device and an external system is provided. Channel selection commands are produced when a scan timer escape interval expires. The channel selection commands each specify a channel in a scan channel list. The scan channel list includes channels selected from a plurality of channels each representing a predetermined frequency band. A channel hopping is performed in response to each of the channel selection commands. The channel hopping makes the channel specified in the each of the channel selection commands an active channel. Data transmission between the implantable medical device and the external system is performed using the active channel during a synchronous scan mode during which the channel hopping in the external system and the channel hopping in the implantable medical device are synchronous. An asynchronous scan mode is started after making a predetermined number of attempts to transmit data using different channels in the scan channel list without success. The synchronization of the channel hopping in the external system and the channel hopping in the implantable medical device is restored during the asynchronous scan mode.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are not necessarily drawn to scale, like numerals describe similar components throughout the several views. The drawings illustrate generally, by way of example, various embodiments discussed in the present document.

DETAILED DESCRIPTION

Figure 1:
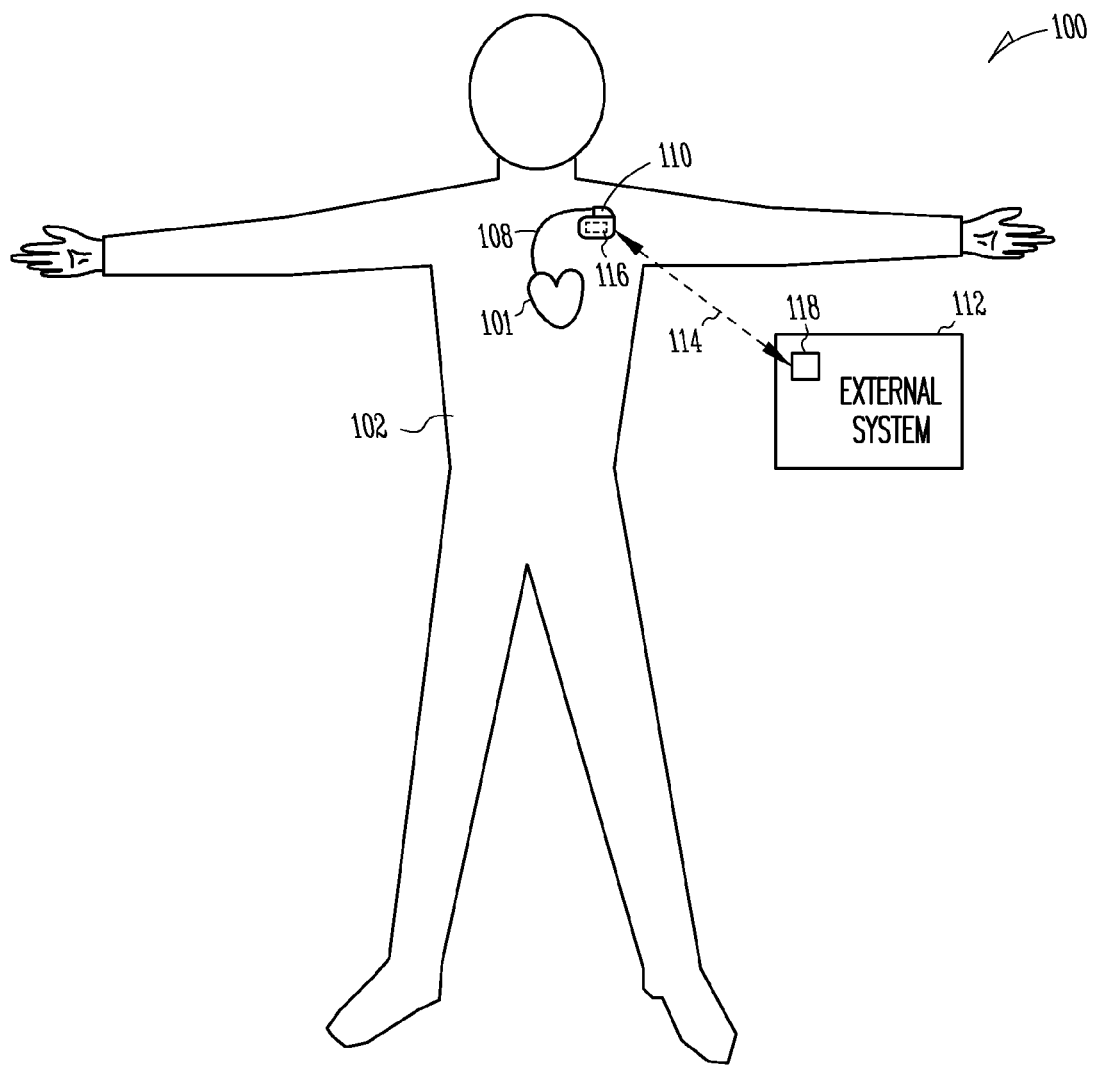
FIG. 1 is an illustration of an embodiment of a CRM system and portions of an environment in which the CRM system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a frequency agile, far-field RF telemetry system for bi-directional communication between an implantable medical device and an external system. The RF telemetry system includes a plurality of channels each representing a frequency band within a predetermined frequency range. Data transmission is performed using an active channel being one of the plurality of channels. Channel hopping is performed on a periodic basis throughout each telemetry session such that the active channel is switched from one channel to another channel over an array of channels selected from the plurality of channels. If a data frame is not successfully transmitted using one channel, it is repeatedly re-transmitted using the current and/or next active channels until its transmission becomes successful. When environmental interference makes one or more channels unusable for data transmission, the channel hopping ensures that the remaining channels are utilized on the periodic basis as the active channel such that the data transmission can continue. The channel hopping is performed at a hopping frequency selected to minimize the duration of interruption to the telemetry when environmental interference is present while providing sufficient time for transmitting data frames using each channel. The channel hopping is normally performed synchronously in the implantable medical device and the external system. If for any reason the channel hopping is out of synchronization, the channel hoping in the external system and the channel hopping in the implantable medical device are performed at substantially different hopping frequencies to allow resynchronization by matching the active channel in the external system to the active channel in the implantable medical device.

While the application in a CRM system is specifically discussed as an example, the present subject matter is applicable to any RF telemetry between an implantable medical device and an external system. The implantable medical device can be any implantable medical device capable of communicating with an external system or device via RF telemetry.

FIG. 1 is an illustration of an embodiment of a CRM system 100 and portions of an environment in which system 100 is used. System 100 includes an implantable medical device 110 and an external system 112. In the illustrated embodiment, after being implanted into a patient's body 102, implantable medical device 110 is coupled to the patient's heart 101 through a lead system 108. In various embodiments, implantable medical device 110 includes one or more of pacemakers, cardioverter/defibrillators, cardiac resynchronization therapy (CRT) devices, cardiac remodeling control therapy (RCT) devices, neural stimulators, drug delivery systems, biological therapy devices, and patient monitoring devices. External system 112 allows a physician or other caregiver to interact with implantable medical device 110 through a telemetry link 114, which provides for bi-directional data communication between implantable medical device 110 and external system 112.

Telemetry link 114 provides for data transmission from implantable medical device 110 to external system 112. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110

(e.g., battery status and lead impedance). Telemetry link 114 also provides for data transmission from external system 112 to implantable medical device 110. This includes, for example, programming implantable medical device 110 to acquire physiological data, programming implantable medical device 110 to perform at least one self-diagnostic test (such as for a device operational status), and programming implantable medical device 110 to deliver at least one therapy.

Telemetry link 114 is a far-field RF telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one embodiment, a communication range of telemetry link 114 (a distance over which data is capable of being wirelessly communicated) is at least ten feet but can be as long as allowed by the communication technology utilized. Unlike an inductive telemetry link using a coil placed near implantable medical device 110, attached to the patient, and electrically connected to external system 112 with a cable, using telemetry link 114 frees the patient from any physical restraints caused by the coil and the cable and allows external system 112 to be placed entirely away from the sterile filed during an operation such as the implantation of implantable medical device 110.

Telemetry link 114 is supported by an implant telemetry module 116 of implantable medical device 110 and an external telemetry module 118 of external system 112. Implant telemetry module 116 and external telemetry module 118 form a frequency agile telemetry system that includes a plurality of channels for data transmission. These channels each represent a frequency band within a predetermined frequency range. The telemetry system performs channel hopping on a periodic basis. In one embodiment, the telemetry system repeatedly selects a channel, uses the selected channel as an active channel for data transmission for about 10-250 ms, and hops to a different channel. The channel hopping is performed synchronously such that implant telemetry module 116 and external telemetry module 118 use the same frequency band for data transmission between them. In one embodiment, implant telemetry module 116 functions as a slave device and external telemetry module 118 functions as a master device. The master device maintains the synchronous channel hopping. When the channel hopping becomes asynchronous, the master device controls a resynchronization process to restore the synchronous channel hopping.

The bi-directional data communication between implantable medical device 110 and external system 112 includes transmission of data frames each being a logic unit of data including a header, a payload, and a trailer. In one embodiment, the header includes a "comma," which includes a unique set of bits for signaling the beginning of receipt of a frame. A lack of comma, or failure to receive the comma, indicates a failure to receive a frame. The payload includes the data block being transmitted. The trailer includes a cyclic redundancy check (CRC) value having a value generated by a transmitter. A receiver receives that CRC value and also recalculates the CRC value based on the received data block and compares the result to the received CRC value in the trailer. The data is deemed to be correctly transmitted if the recalculated CRC value matches the received CRC value. A CRC error refers to a mismatch between the recalculated CRC value and the received CRC value. Depending on the specific communication formats, the header and the trailer each include additional information for flagging, control of data recovery, and/or synchronization between implant telemetry module 116 and external telemetry module 118. In various embodiments, data frame exchange errors, such as comma errors and CRC errors, indicate a need for re-transmission of the same data frame using the current and/or next active channels.

In one embodiment, external system 112 includes a programmer. In another embodiment, external system 112 includes a patient management system including an external device, a telecommunication network, and one or more remote devices. The external device is placed within the vicinity of implantable medical device 110 and includes external telemetry module 118 to communicate with implantable medical device 110 via telemetry link 114. The one or more remote devices are in one or more remote locations and communicate with the external device through the telecommunication network, thus allowing the physician or other caregiver to monitor and treat the patient from a distant location and/or allowing access to various treatment resources from the one or more remote locations.

Figure 2:
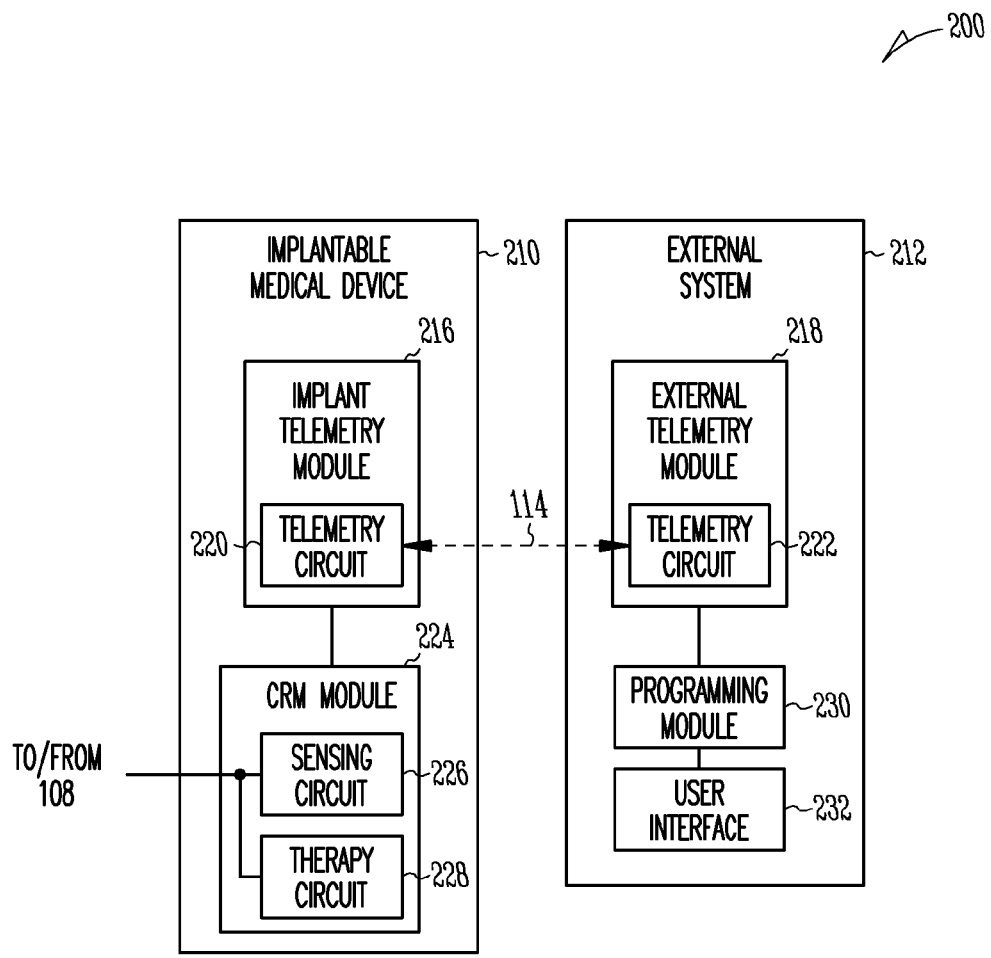
FIG. 2 is a block diagram illustrating an embodiment of a circuit of the CRM system.

FIG. 2 is a block diagram illustrating an embodiment of a circuit of a CRM system 200, which is a specific embodiment of CRM system 100. System 200 includes an implantable medical device 210, an external system 212, and telemetry link 114 providing for communication between implantable medical device 210 and external system 212.

Implantable medical device 210 is a specific embodiment of implantable medical device 110 and includes an implant telemetry module 216 and a CRM module 224. CRM module 224 includes a sensing circuit 226 that senses one or more physiological signals and a therapy circuit 228 that delivers one or more cardiac therapies. In various embodiments, therapy circuit 228 includes one or more of a pacing circuit, a cardioversion/defibrillation circuit, CRT circuit, RCT circuit, and any other circuit that delivers a cardiac therapy. In one specific embodiment, therapy circuit 228 delivers cardiac electrical stimulation pulses such as pacing and cardioversion/defibrillation pulses. In various embodiments, CRM module 224 further includes one or more of a drug delivery device and a biologic therapy device.

External system 212 is a specific embodiment of external system 112 and includes an external telemetry module 218, a programming module 230, and a user interface 232. Programming module 230 allows for processing of data transmitted from implantable medical device 210 via telemetry link 114 and programming of implantable medical device 210 by transmitting instructions via telemetry link 114. User interface 232 allows the physician or other caregiver to observe and analyze physiological signals and device operation data transmitted from implantable medical device 210 and to adjust the operation of implantable medical device 210.

Implant telemetry module 216 includes a telemetry circuit 220. External telemetry module 218 includes a telemetry circuit 222. Telemetry circuits 220 and 222 are discussed in detail below, with reference to FIGS. 4 and 5.

In various embodiments, the system elements, including various modules and circuits, described in this document are implemented by hardware, software, firmware, or any combination thereof. In various embodiments, the circuits or portions thereof described in this document are each an application-specific circuit constructed to perform one or more particular functions, a general-purpose circuit programmed to perform such function(s), or a combination thereof.

Figure 3:
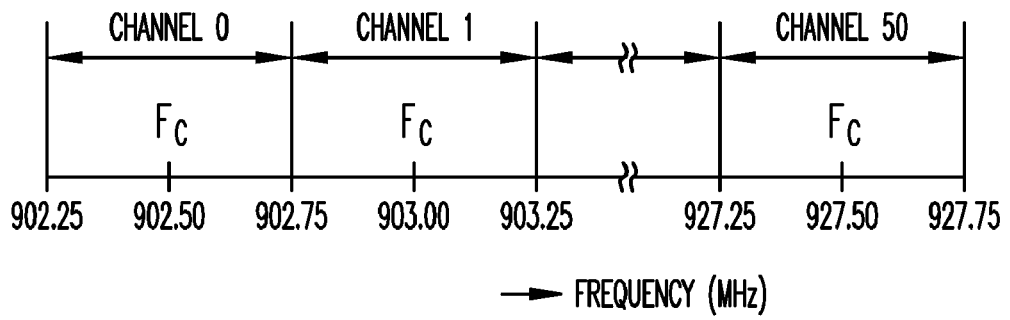
FIG. 3 is an illustration of an embodiment of telemetry channels (frequency bands) for data transmission between an implantable medical device and an external system of the CRM system.

FIG. 3 is an illustration of an embodiment of the plurality of channels for data transmission via telemetry link 114. The channels are distributed continuously over the predetermined frequency range. As illustrated in FIG. 3, an example of the predetermined frequency range is approximately 902.25-927.75 MHz. Each channel has a center (carrier) frequency and a bandwidth of approximately 500 kHz. Thus, the plurality of channels includes 51 channels each having a 500-kHz bandwidth within the frequency range of 902.25-927.75 MHz, within the Industrial, Scientific and Medical (ISM) band of the United States. The center frequency for each channel is approximately the mid-point of the frequency band represented by that channel. In the illustrated embodiment, Channel 0 has a frequency band of 902.25-902.75 MHz and a center frequency of 902.50 MHz, Channel 1 has a frequency band of 902.75-903.25 MHz and a center frequency of 903.00 MHz, and so forth. Other examples of the predetermined frequency range include approximately 863.0-870.0 MHz, within the Short Range Device (SRD) band of the European Union, approximately 402.0-405.0 MHz, within the worldwide Medical Implant Communication Service (MICS) band, and approximately 420.0-430.0 MHz and 440.0-450.0 MHz, within the available bands in Japan.

Figure 4:
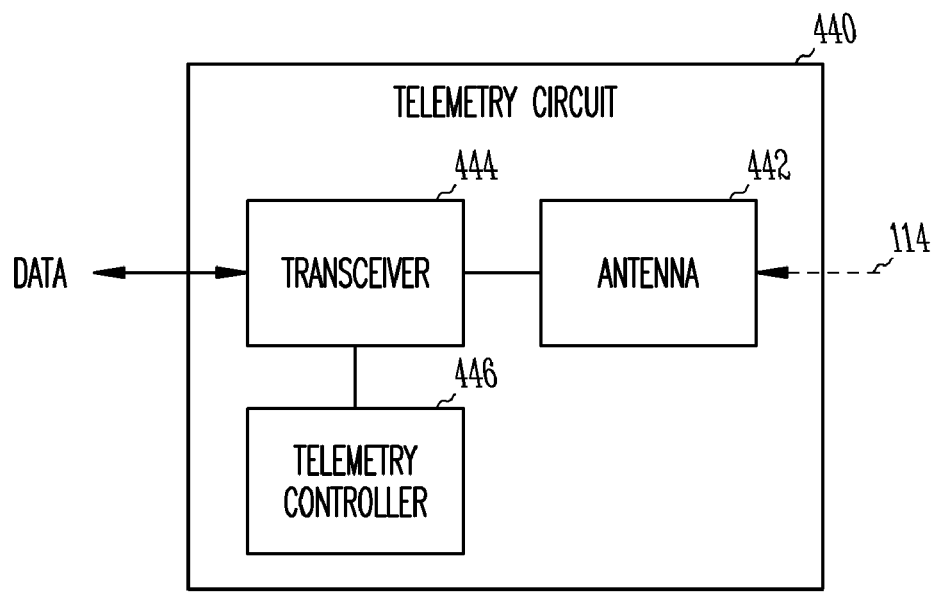
FIG. 4 is a block diagram illustrating an embodiment of a telemetry circuit of the CRM system.

FIG. 4 is a block diagram illustrating an embodiment of a telemetry circuit 440. Telemetry circuit 440 represents a specific embodiment of telemetry circuit 220 and/or telemetry circuit 222. In various embodiments, telemetry circuit 220 and telemetry circuit 222 each include a telemetry circuit illustrated as telemetry circuit 440 and discussed in this document.

Telemetry circuit 440 includes an antenna 442, a transceiver 444, and a telemetry controller 446. Transceiver 444 transmits and receives data through antenna 442 using at least one active channel during a telemetry session. The active channel is selected from the plurality of channels each representing a predetermined frequency band for data transmission via telemetry link 114. Telemetry controller 446 controls channel hopping on a periodic basis. The channel hopping includes selecting the active channel from the plurality of channels. After an active channel is selected, telemetry controller 446 controls the data transmission using the active channel during a synchronous scan mode, during which the channel hopping in the external system and the channel hopping in the implantable medical device are synchronous. If the channel hopping in the external system and the channel hopping in the implantable medical device become asynchronous, telemetry controller 446 starts an asynchronous scan mode. During the asynchronous scan mode, telemetry controller 446 restores the synchronization of the channel hopping in the external system and the channel hopping in the implantable medical device.

Figure 5:
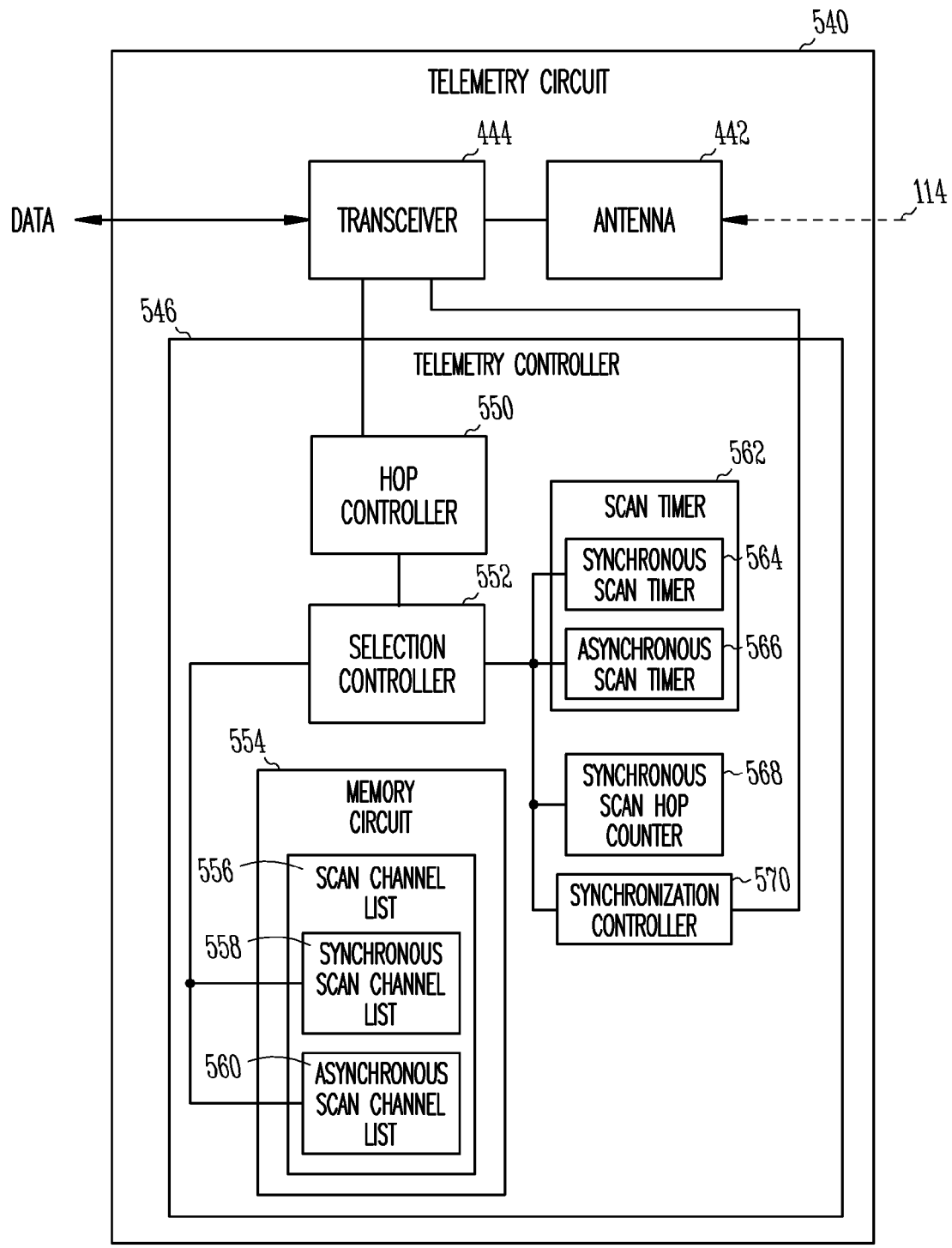
FIG. 5 is a block diagram illustrating a specific embodiment of the telemetry circuit.

FIG. 5 is a block diagram illustrating an embodiment of a telemetry circuit 540, which is specific embodiment of telemetry circuit 440. Telemetry circuit 540 includes antenna 442, transceiver 444, and a telemetry controller 546. Telemetry controller 546 includes a hop controller 550, a selection controller 552, a memory circuit 554, a scan timer 562, a synchronous scan hop counter 568, and a synchronization controller 570.

Selection controller 552 produces channel selection commands each specifying a channel in the scan channel list when a scan timer escape interval expires. Hop controller 550 controls a channel hopping in response to each of the channel selection commands. The channel hopping makes the channel specified in the each of the channel selection commands the active channel for the data transmission via telemetry link 114. During the synchronous scan mode, selection controller 552 produces each of the channel selection commands when a synchronous scan timer escape interval expires. The channel selection commands specify the channels in a synchronous hopping sequence. During the asynchronous scan mode, selection controller 552 produces each of the channel selection commands when an asynchronous scan timer escape interval expires. The channel selection commands specify the channels in an asynchronous hopping sequence.

Memory circuit 554 stores a scan channel list 556, which is the scan channel list including the channels specified in the channel selection commands. Scan channel list 556 includes a synchronous scan channel list 558 and an asynchronous scan channel list 560. Synchronous scan channel list 558 includes a first array of channels listed in the synchronous hopping sequence. Asynchronous scan channel list 560 includes a second array of channels listed in the asynchronous hopping sequence. Selection controller 552 produces the channel selection commands specifying the channels in synchronous scan channel list 558 during the synchronous scan mode, and produces the channel selection commands specifying the channels in asynchronous scan channel list 560 during the asynchronous scan mode. In one embodiment, the first array of channels including all the channels of the plurality of channels. In another embodiment, the first array of channels includes preferred channels selected from the plurality of channels. In one embodiment, the second array of channels is a subset of the first array of channels.

Scan timer 562 times the scan timer escape interval. Scan timer 562 includes a synchronous scan timer 564 and an asynchronous scan timer 566. Synchronous scan timer 564 times the synchronous scan timer escape interval during the synchronous scan mode. In one embodiment, the synchronous scan timer escape interval is between approximately 10 and 250 ms. Asynchronous scan timer 566 times the asynchronous scan timer escape interval during the asynchronous scan mode. In one embodiment, the asynchronous scan timer escape interval of external telemetry module 218 has a length allowing external telemetry module 218 to hop through all channels of its asynchronous scan channel list 560 during each asynchronous scan timer escape interval of implant telemetry module 216. This allows external telemetry module 218 to scan all the channels in its asynchronous scan channel list 560 against each channel of the asynchronous scan channel list 560 of implant telemetry module 216 until the channels are matched in the external telemetry module 218 and implant telemetry module 216.

Synchronous scan hop counter 568 counts a synchronous scan hop count during the synchronous scan mode. When the synchronous scan hop count reaches a predetermined maximum hop count, synchronous scan hop counter 568 starts the asynchronous scan mode. The synchronous scan hop count is incremented each time when the synchronous scan timer escape interval expires and is reset by a signal indicative of successful data transmission. In other words, when the number of channels attempted to transmit the same data frame without success reaches the predetermined maximum hop count, synchronous scan hop counter 568 starts the asynchronous scan mode.

During the synchronous scan mode, synchronization controller 570 maintains the synchronization of the channel hopping in external telemetry module 218 and implant telemetry module 216. During the asynchronous scan mode, synchronization controller 570 restores the synchronization of the channel hopping in external telemetry module 218 and implant telemetry module 216 to re-enter the synchronous scan mode.

In one embodiment, implant telemetry module 216 functions as a slave device and external telemetry module 218 functions as a master device in maintaining and restoring the synchronization of the channel hopping. Synchronization controller 570 of external telemetry module 218 transmits selected channel selection commands according to a predetermined synchronization-maintenance schedule to implant telemetry module 216. Synchronization controller 570 of implant telemetry module 216 receives these commands and adjusts synchronous scan timer 564 of implant telemetry module 216 when necessary to maintain the synchronization of the channel hopping. In one embodiment, synchronization controller 570 of external telemetry module 218 transmits information specifying the content of scan channel list 556. Synchronization controller 570 of implant telemetry module 216 receives the information and updates scan channel list 556 of implant telemetry module 216 accordingly. During the asynchronous scan mode, synchronization controller 570 of external telemetry module 218 transmits a scan command to implant telemetry module 216 using each channel while the channels are scanned. Synchronization controller 570 of implant telemetry module 216 sends a response to the scan command when it receives the scan command. The channel hopping is resynchronized when the response to the scan command is received by external telemetry module 218. The reception of the response to the scan command indicates a match between the active channels of external telemetry module 218 and implant telemetry module 216.

Figure 6A:
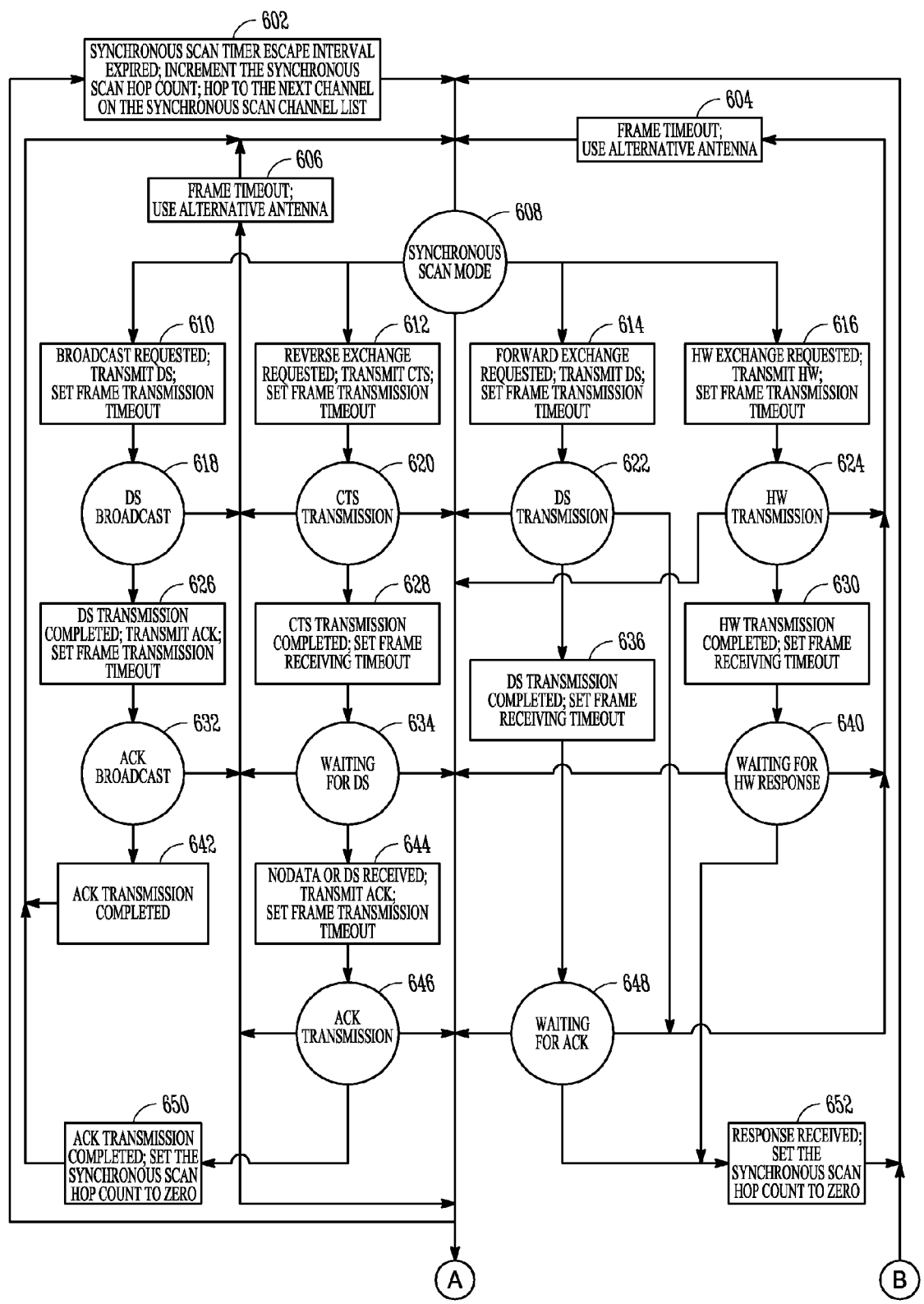
FIGS. 6A and FIG. 6B illustrate a state diagram of an example of an embodiment of frequency hopping in an external system communicating with an implantable medical device.
Figure 6B:
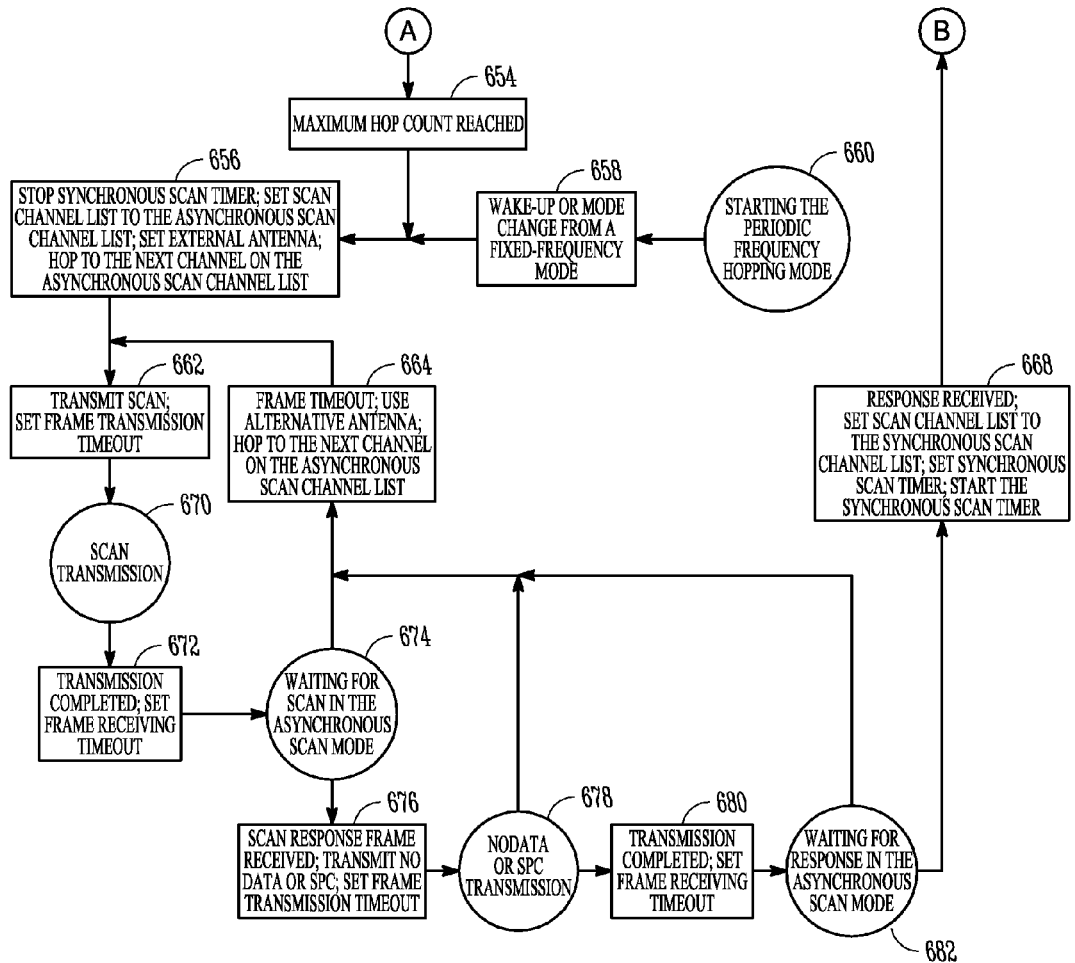
Figure 7:
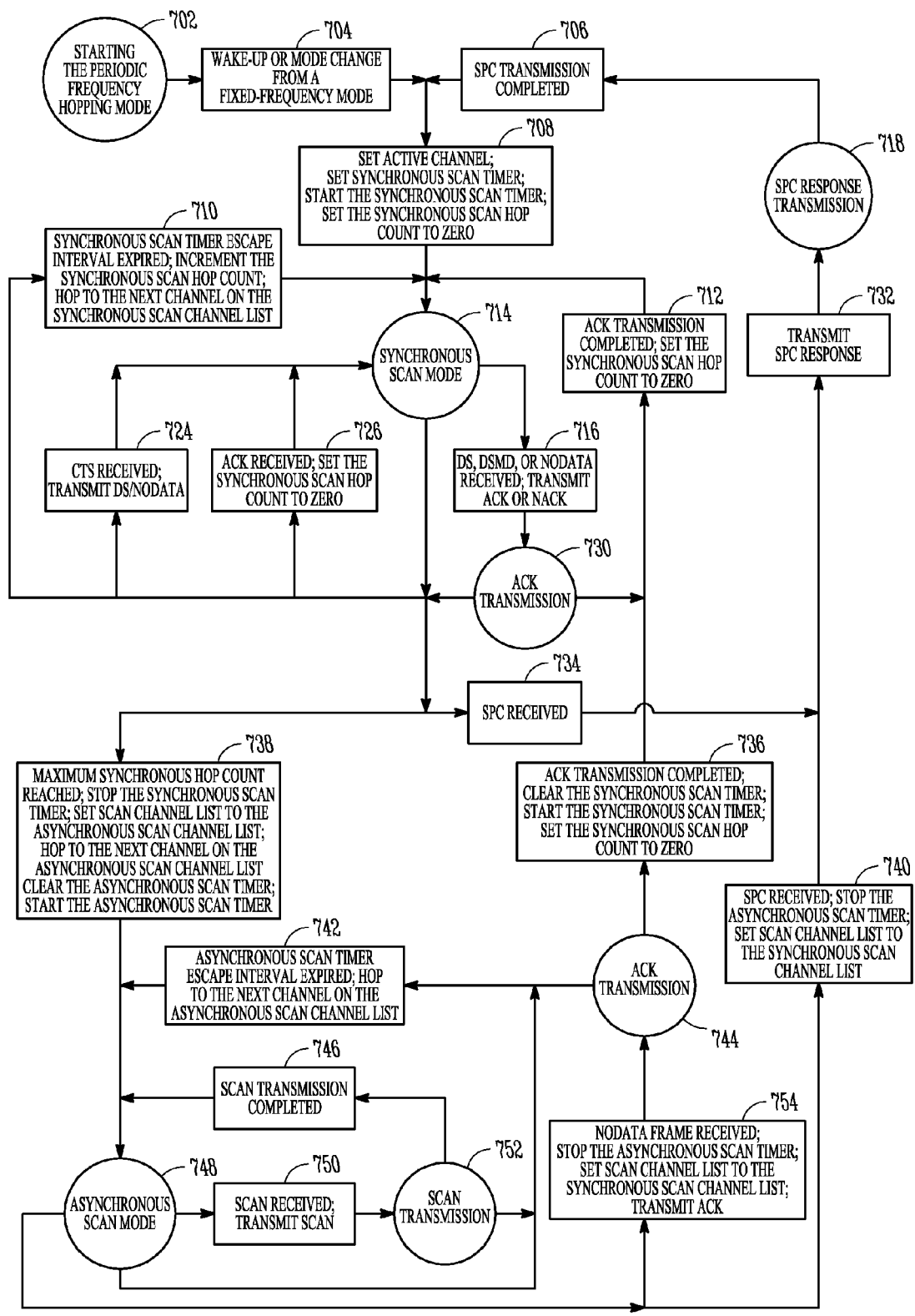
FIG. 7 is a state diagram illustrating a specific embodiment of frequency hopping in the implantable medical device communicating with the external system.

FIGS. 6A, 6B, and 7 illustrate state diagrams examples of frequency hopping in a telemetry system providing for communication between an implantable medical device and an external system. FIG. 6A and FIG. 6B illustrate a state diagram of an example of embodiment of frequency hopping in the external system. FIG. 7 is a state diagram illustrating an example of frequency hopping in the implantable medical device. The following is a list of description of states and acts represented by reference numbers in FIGS. 6A, 6B, and 7:

FIG. 6A and FIG. 6B (the external system):
602: Synchronous scan timer escape interval expired;
Increment the synchronous scan hop count;
Hop to the next channel on the synchronous scan channel list.
604: Frame timeout;
Use alternative antenna.
606: Frame timeout;
Use alternative antenna.
608: Synchronous scan mode.
610: Broadcast requested;
Transmit DS (Data Send frame);
Set frame transmission timeout.
612: Reverse exchange requested;
Transmit CTS (Clear To Send frame);
Set frame transmission timeout.
614: Forward exchange requested;
Transmit DS;
Set frame transmission timeout.
616: HW (HardWare frame, processed directly by hardware) exchange requested;
Transmit HW;
Set frame transmission timeout.
618: DS broadcast.
620: CTS transmission.
622: DS transmission.
624: HW transmission.
626: DS transmission completed;
Transmit ACK (ACKnowledge frame);
Set frame transmission timeout.
628: CTS transmission completed;
Set frame receiving timeout.
630: HW transmission completed;
Set frame receiving timeout.
632: ACK broadcast.
634: Waiting for DS.
636: DS transmission completed;
Set frame receiving timeout.
640: Waiting for HW response.
642: ACK transmission completed.
644: NODATA (frame indicating NO DATA to send) or DS received;
Transmit ACK;
Set frame transmission timeout.
646: ACK transmission.
648: Waiting for ACK.
650: ACK transmission completed;
Set the synchronous scan hop count to zero.
652: Response received;
Set the synchronous scan hop count to zero.
654: Maximum hop count reached.
656: Stop synchronous scan timer;
Set scan channel list to the asynchronous scan channel list;
Set external antenna;
Hop to the next channel on the asynchronous scan channel list.
658: Wake-up or mode change from a fixed-frequency mode.
660: Starting the periodic frequency hopping mode.
662: Transmit SCAN;
Set frame transmission timeout.
664: Frame timeout;
Use alternative antenna;
Hop to the next channel on the asynchronous scan channel list (after using all antennas).
668: Response received;
Set scan channel list to the synchronous scan channel list;
Set synchronous scan timer;
Start the synchronous scan timer.
670: SCAN transmission.
672: Transmission completed;
Set frame receiving timeout.
674: Waiting for SCAN in the asynchronous scan mode.
676: SCAN response frame received;
Transmit NODATA or SPC (Set Primary [i.e., active] Channel frame);
Set frame transmission timeout.
678: NODATA or SPC transmission.
680: Transmission completed;
Set frame receiving timeout.
682: Waiting for response in the asynchronous scan mode.
FIG. 7 (the implantable medical device):
702: Starting the periodic frequency hopping mode.
704: Wake-up or mode change from a fixed-frequency mode.
706: SPC transmission completed.
708: Set active channel;
Set synchronous scan timer;
Start the synchronous scan timer;
Set the synchronous scan hop count to zero.
710: Synchronous scan timer escape interval expired;
Increment the synchronous scan hop count;
Hop to the next channel on the synchronous scan channel list.
712: ACK transmission completed;
Set the synchronous scan hop count to zero.
714: Synchronous scan mode.

716: DS, DSMD (Data Send with More Data frame), or NODATA received;
  Transmit ACK or NACK (No ACKnowledgement frame, indicating that a message is received but unable to process at the moment).
718: SPC response transmission.
724: CTS received;
  Transmit DS/NODATA.
726: ACK received;
  Set the synchronous scan hop count to zero.
730: ACK transmission.
732: Transmit SPC response.
734: SPC received.
736: ACK transmission completed;
  Clear the synchronous scan timer;
  Start the synchronous scan timer;
  Set the synchronous scan hop count to zero.
738: Maximum synchronous hop count reached;
  Stop the synchronous scan timer;
  Set scan channel list to the asynchronous scan channel list;
  Hop to the next channel on the asynchronous scan channel list.
  Clear the asynchronous scan timer;
  Start the asynchronous scan timer;
740: SPC received;
  Stop the asynchronous scan timer;
  Set scan channel list to the synchronous scan channel list;
742: Asynchronous scan timer escape interval expired;
  Hop to the next channel on the asynchronous scan channel list.
744: ACK transmission.
746: SCAN transmission completed.
748: Asynchronous scan mode.
750: SCAN received;
  Transmit SCAN.
752: SCAN transmission.
754: NODATA frame received;
  Stop the asynchronous scan timer;
  Set scan channel list to the synchronous scan channel list;
  Transmit ACK.

In one embodiment, the state diagrams of FIGS. 6A, 6B, and 7 are implemented in system 100, including its specific embodiment system 200. The state diagram of FIGS. 6A and 6B is implemented using telemetry controller 446 of telemetry circuit 222. The state diagram of FIG. 7 is implemented using telemetry controller 446 of telemetry circuit 220. These state diagrams are discussed using various scenarios below.

Scenarios 1-12 apply to the operation of the telemetry system while in the synchronous scan mode and the transition to the asynchronous scan mode. During the synchronous scan mode, the external system and implantable medical device hop channels in synchronization. The synchronization is maintained by transmission of a SPC (Set Primary [i.e., active] Channel) frame from the external system to the implantable medical device. The SPC frame includes the channel selection command discussed above.

Scenarios 1-3 are scenarios of "forward data exchange", which refers to data exchange for transmitting information from the external system to the implantable medical device.

Under scenario 1, a complete forward data exchange occurs with sufficient time for the exchange to occur using the current active channel. To send data to the implantable medical device, the external system first checks that a complete frame exchange can be completed in the time remaining on the current active channel. The amount of time required is based on the amount of data to be transferred and for receiving an ACK (ACKnowledgement) frame from the implantable medical device. When there is sufficient amount of time for the complete frame exchange, the external system transmits the data in a DS (Data Send) frame to the implantable medical device, starts an ACK timeout, and then waits up to this amount of time for the implantable medical device to respond. Having received the DS frame, the implantable medical device responds with the ACK frame. After transmitting the ACK frame, the implantable medical device resets its synchronous scan hop count. Having received the ACK from the implantable medical device within the ACK timeout, the external system resets its synchronous scan hop count. Both the implantable medical device and the external system return to synchronous scan mode and the forward data exchange is complete.

Under scenario 2, the implantable medical device does not receive the DS frame sent from the external system. The external system starts the forward data exchange by sending the DS frame to the implantable medical device. If the DS frame is not successfully received, the implantable medical device does not transmit the ACK frame to the external system, does not reset its synchronous scan hop count, and stays in the synchronous scan mode. If the ACK frame is not received before the ACK timeout expires, the external system returns to the synchronous scan mode without resetting its synchronous scan hop count. The external system then evaluates the pending requests for data transmission for the highest priority request. The forward data exchange continues to be attempted on the current active channel until the synchronous scan timer escape interval expires. When the synchronous scan timer escape interval expires, the active channel hops to the next channel on the synchronous scan channel list in each of the external system and the implantable medical device simultaneously. The forward data exchange is then attempted using the new active channel. If the forward data exchange continues to fail after a maximum number of channel hopping have occurred, the external system and the implantable medical device both enter the asynchronous scan mode. This maximum number is programmable.

Under scenario 3, the external system does not receive the ACK frame sent from the implantable medical device. The external system sends data to the implantable medical device in a DS frame and starts the ACK timeout. The implantable medical device receives the data without error, sent the ACK frame, resets its synchronous scan hop count, and returns to the synchronous scan mode. The external system does not receive the frame ACK frame, so it does not reset its synchronous scan hop count. After the ACK timeout expires, the external system returns to the synchronous scan mode and evaluates the pending requests for data transmission for the highest priority request. The forward data exchange is then attempted again. If this error persists until the synchronous scan timer escape interval expires, the active channel hops to the next channel on the synchronous scan channel list in each of the external system and the implantable medical device simultaneously. The external system attempts the forward data exchange using the new active channel. If no interfering signal is present at the frequency band represented by this new active channel, the forward data exchange is likely to go through. If the implantable medical device receives the same DS frame more than once, it filters out the duplicated data. If the forward data exchange continues to fail after a maximum number of channel hopping have occurred in the external system, the external system enters the asynchronous scan mode, but the implantable medical device remains in the synchronous scan mode. The external system then begins scanning for a new active channel by sending a SCAN frame to the implantable medical device. The implantable medical device does not respond to the SCAN frame and eventually reaches a maximum scan count and enters the asynchronous scan mode.

Scenarios 4-7 are scenarios of "reverse data exchange", which refers to data exchange for transmitting information from the implantable medical device to the external system, when the implantable medical device has data to transmit.

Under scenario 4, a complete reverse data exchange occurs with sufficient time for the exchange to occur using the current active channel. Reverse data exchanges are performed for one of two reasons. The first reason is the periodic polling by the external system. The implantable medical device responds to the polling by sending data, if it has data to send. The polling rate is primarily chosen to retrieve real time data from the implantable medical device. The second reason is that in a previous frame exchange, the implantable medical device indicated that it had more data to send. The external system initiates a reverse data exchange by sending a CTS (Clear To Send) frame to the implantable medical device. After sending the CTS frame, the external system starts a DS timeout and waits to receive a DS, DSMD (Data Send with More Data), or NODATA (indicating no data to send) frame from the implantable medical device. In response to the reception of the CTS frame from the external system, the implantable medical device sends the highest priority data available in the DS frame. In response to the reception of the DS or DSMD frame, the external system sends an ACK frame to the implantable medical device and resets its synchronous scan hop count. In response to the reception of the ACK frame, the implantable medical device resets its synchronous scan hop. The implantable medical device then discards the data in the previous DS or DSMD frame because the external system has received the data.

Under scenario 5, the implantable medical device fails to receive the CTS frame from the external system. The external system sends the CTS frame to the implantable medical device and starts the DS timeout. Because the CTS frame is not received, the implantable medical device does not send the DS, DSMD, or NODATA frame and remains in the synchronous scan mode. When the DS timeout expires in the external system, the reverse data exchange is declared a failed attempt, and the external system returns to the synchronous scan mode. The external system then evaluates the pending requests for data transmission for the highest priority request. Since the ACK frame was not transmitted or received, neither the external system nor the implantable medical device resets the synchronous scan hop count. Because the external system does not know whether the implantable medical device has data to be transmitted, the poll for data request remains active, and the external system starts the reverse data exchange again. Thus, the reverse data exchange continues to be attempted using the current active channel until the synchronous scan timer escape interval expires. When the synchronous scan timer escape interval expires, the active channel hops to the next channel on the synchronous scan channel list in each of the external system and the implantable medical device simultaneously. The reverse data exchange is then attempted using the new active channel. If the reverse data exchange continues to fail after the maximum number of channel hopping have occurred, the external system and the implantable medical device both enter the asynchronous scan mode.

Under scenario 6, the external system fails to receive the DS, DSMD, or NODATA frame. The external system sends the CTS frame to the implantable medical device and starts the DS timeout. After the CTS frame is successfully received from the external system, the implantable medical device sends the DS, DSMD, or NODATA frame. The external system fails to receive the DS, DSMD, or NODATA frame, and therefore does not send the ACK frame to the implantable medical device. If the DS, DSMD, or NODATA frame is not received before the DS timeout expires, the external system returns to the synchronous scan mode. The external system then evaluates the pending requests for data transmission for the highest priority request. The implantable medical device holds the data in the DS frame for transmission in response to a future CTS frame sent from the external system. Because the ACK frame is not transmitted or received, neither the external system of the implantable medical device resets its synchronous scan hop count. The external system thus attempts the reverse data exchange again using the current active channel until the synchronous scan timer escape interval expires. When the synchronous scan timer escape interval expires, the active channel hops to the next channel on the synchronous scan channel list in each of the external system and the implantable medical device simultaneously. The reverse data exchange is then attempted using the new active channel. If the reverse data exchange continues to fail after the maximum number of channel hopping have occurred, the external system and the implantable medical device both enter the asynchronous scan mode.

Under scenario 7, the implantable medical device does not receive the ACK frame. In response to the successful reception of the DS, DSMD, or NODATA frame, the external system sends the ACK frame to the implantable medical device. Because the implantable medical device does not receive the ACK frame, it holds the data in the DS frame for transmission in response to the future CTS frame sent from the external system. In the future exchange, the external system receives the data in a duplicate DS frame and discards the data.

Scenarios 8-10 are scenarios of the reverse data exchange when the implantable medical device has no data to transmit.

Under scenario 8, a complete reverse data exchange occurs when the implantable medical device has no data to be sent to the external system. The external system initiates the reverse data exchanges by sending the CTS frame to the implantable medical device. The external system then starts the DS timeout and waits for the DS, DSMD, or NODATA frame from the implantable medical device. In response to the reception of the CTS frame, the implantable medical device that has no data to send responds by sending the NODATA frame. In response to the reception of the NODATA frame, the external system sends the ACK frame to the implantable medical device. After transmitting the ACK frame, the implantable medical device resets its synchronous scan hop count. Having received the ACK from the implantable medical device within the ACK timeout, the external system resets its synchronous scan hop count.

Under scenario 9, the external system fails to receive the NODATA frame. In response to the reception of the CTS frame from the external system, the implantable medical device sends the NODATA frame to the external system. Because the external system does not receive the NODATA frame, it does not send the ACK frame to the implantable medical device. If the NODATA frame is not received before the DS timeout expires, the external system returns to the synchronous scan mode. Because the external system does not know whether the implantable medical device has data to send, it immediately polls the implantable medical device for data again.

Under scenario 10, the implantable medical device fails to receive the ACK frame sent from the external system. The external system sent the CTS frame. In response, the implantable medical device sends the DS, DSMD, or NODATA frame, and the external system receives that frame. The external system then sends the ACK frame and resets its synchronous scan hop count. The implantable medical device does not receive the ACK frame, so it does not reset its synchronous scan hop count. When the synchronous scan timer escape interval expires, the active channel hops to the next channel on the synchronous scan channel list in each of the external system and the implantable medical device simultaneously. The reverse data exchange is then attempted using the new active channel. If the implantable medical device continues to fail to receive the ACK frame after it has reached the maximum number of channel hopping, the implantable medical device enters the asynchronous scan mode while the external system remains in the synchronous scan mode. The implantable medical device then responds only to the SCAN, NODATA, and SPC frames. The external system keeps transmitting the CTS frames until it also reaches the maximum hop count and enters the asynchronous scan mode.

Scenarios 11 and 12 are scenarios of prolonged interruption of data transmission between the implantable medical system and the external system.

Under scenario 11, the synchronous scan timer escape interval expires. When the synchronous scan timer escape interval expires, the external system and the implantable medical device each hop to the next channel on its synchronous scan list, and the external system initiates a new frame exchange. The external system is to ensure that a complete forward data exchange or reverse data exchange completes within the remaining synchronous scan timer escape interval on the current active channel. When the synchronous scan timer escape interval expires, and the synchronous scan hop count has reached the maximum hop count, both the external system and the implantable medical device enter the asynchronous scan mode.

Under scenario 12, the synchronous scan timers in the external system and implantable medical device are synchronized. Due to the slight drift expected between the clocks in the external system and implantable medical device that drive the synchronous scan timers, the external system periodically sends the SPC frame to the implantable medical device. The SPC frame contains information specifying the channel in the channel hoping list to which the implantable medical device is to hop as well as the synchronous scan timer escape interval for loading into the synchronous scan timer of the implantable medical device. When the implantable medical device receives the SPC frame, it sends a SPC response frame to the external system, hops to the specified channel (the new active channel), and starts the synchronous scan timer. In response to the reception of the SPC response frame, the external system hops to the new channel and also starts its synchronous scan timer. The synchronous scan timer escape interval of the external system and the synchronous scan timer escape interval in the implantable medical device are set to the same value, which is determined or adjusted based on experimental data based on the actual timing behavior of the implantable medical device.

Scenarios 13-17 apply to the operation of the telemetry system while in the asynchronous scan mode and the transition back to synchronous scan mode. During the asynchronous scan mode, the external system and implantable medical device hop channels at different hopping frequencies. In this mode, the external system scans through all channels in an asynchronous scan list at least once while the implantable medical device stays in the same active channel.

Under scenario 13, an exchange of a SCAN and SCAN response frames and an exchange of the NODATA and ACK frames are successful. This is the normal case for transitioning from the asynchronous scan mode back to synchronous scan mode. The external system sends the SCAN frame to the implantable medical device. In response, the implantable medical device sends a SCAN response frame, and the external system receives the SCAN response frame without error. At this time, the external system learns the frequency band of the current active channel in the implantable medical device and modifies its asynchronous scan channel list such that the current active channel in the implantable medical device becomes the next on the asynchronous scan channel list. This completes an intermediate synchronization of the asynchronous scan channel lists in the external system and the implantable medical device. The external system then sends the NODATA frame to the implantable medical device. In response to the successful reception of the NODATA frame, the implantable medical device sends the ACK frame to the external system, resets its synchronous scan hop count at the end of the ACK frame transmission, and returns to the synchronous scan mode. In response to the successful reception of the ACK frame, the external system resets its synchronous scan hop count and enters the synchronous scan mode.

Under scenario 14, the exchange of the SCAN and SCAN response frames is successful, and the implantable medical device sends the ACK frame, but the external system fails to receive the ACK frame. The external system sends the SCAN frame to the implantable medical device. In response, the implantable medical device sends a SCAN response frame, and the external system receives the SCAN response frame without error. At this time, the external system learns the frequency band of the current active channel in the implantable medical device and modifies its asynchronous scan channel list such that the current active channel in the implantable medical device becomes the next on the asynchronous scan channel list. This completes an intermediate synchronization of the asynchronous scan channel lists in the external system and the implantable medical device. The external system then sends the NODATA frame to the implantable medical device. In response to the successful reception of the NODATA frame, the implantable medical device sends the ACK frame to the external system, resets its synchronous scan hop count at the end of the ACK frame transmission, and returns to the synchronous scan mode. The external system fails to receive the ACK frame successfully, so it transmits a subsequent SCAN frame after a SCAN timeout expires, and remains in the asynchronous scan mode. Because the external system has modified the asynchronous scan channel, it is on the same active channel as the implantable medical device. The implantable medical device sends the SCAN response frame. The external system then sends the NODATA frame to the implantable medical device. In response to the successful reception of the NODATA frame, the implantable medical device sends the ACK frame to the external system, resets its synchronous scan hop count at the end of the ACK frame transmission, and returns to the synchronous scan mode. If the external system successfully receives the ACK frame this time, it returns to the synchronous scan mode. If the external system continues to fail to receive the ACK frame, it remains in the asynchronous scan mode while the implantable medical device is in the synchronous scan mode. Thus, the external system hops through its asynchronous scan list, and the implantable medical device hops through its synchronous scan list. Given that the external system and the implantable medical device have the identical scan channel lists, and the asynchronous channel scan list is a subset of the synchronous scan channel list, the external system and the implantable medical device may hop to the same channel before the synchronous scan hop count reaches the maximum hop count in the implantable medical device. If the exchange of the SCAN and SCAN response frames and the exchange of the NODATA and ACK frames are not successfully completed before the synchronous scan hop count reaches the maximum hop count, the implantable medical device falls back to the asynchronous scan mode.

Under scenario 15, the SCAN and SCAN response frame exchange is successful, but the implantable medical device fails to receive the NODATA frame. The external system sends the SCAN frame to the implantable medical device. In response, the implantable medical device sends a SCAN response frame, and the external system receives the SCAN response frame without error. At this time, the external system learns the frequency band of the current active channel in the implantable medical device and modifies its asynchronous scan channel list such that the current active channel in the implantable medical device becomes the next on the asynchronous scan channel list. This completes an intermediate synchronization of the asynchronous scan channel lists in the external system and the implantable medical device. The external system then sends the NODATA frame to the implantable medical device. Because the implantable medical device fails to receive the NODATA frame, it does not transmit the ACK frame to the external system and remains in the asynchronous scan mode. Because the external system does not receive the ACK frame, it also remains in the asynchronous scan mode. The external system then resumes scanning channels in the asynchronous scan channel list starting with the current active channel in the implantable medical device.

Under scenario 16, the external system fails to receive the SCAN response frame from the implantable medical device. The external system sends the SCAN frame to the implantable medical device. In response, the implantable medical device sends a SCAN response frame, but the external system fails to receive the SCAN response frame. Both the external system and the implantable medical device remain in the asynchronous mode and resume scanning channels from their asynchronous scan lists without the intermediate synchronization of the asynchronous scan channel lists.

Under scenario 17, the implantable medical device fails to receive the SCAN frame. The external system sends the SCAN frame, but the implantable medical device fails to receive the SCAN frame. The implantable medical device does not respond. Both the external system and the implantable medical device continue to scan channels from their asynchronous scan lists without the intermediate synchronization of the asynchronous scan channel lists.

In an alternative embodiment that applies to scenarios 13-17 as discussed above, the SPC frame replaces the NODATA frame, and the SPC response frame replaces the ACK frame. This alternative embodiment does not affect the results of the operation of the telemetry system while in the asynchronous scan mode and the transition back to synchronous scan mode.

In an alternative embodiment, instead of performing a complete forward or reverse data exchange using one active channel, the data exchange is allowed to be completed using two or more active channels. For example, if a data exchange is requested while there is insufficient time for the data exchange to be completed using the current active channel, the data exchange occurs using the current and the next active channels. In one embodiment, a "delay during frame transmission" mode is applied to transmission of selected or all frames discussed above. The delay during frame transmission mode delays a scheduled channel hopping, such as by temporarily extending the synchronous scan timer escape interval, to ensure that an ongoing transmission of a data frame is completed before the channel hopping. The transmission of the next data frame is performed after the channel hopping. The delay during frame transmission mode maximizes the waiting time for the data exchange, thereby increasing the efficiency of telemetry and potentially reducing the required length of a telemetry session.

In one embodiment, to maintain synchronization of timers in the external system and the implantable medical device, exchanges of the SPC and SPC response frames are performed according to a predetermined synchronization-maintenance schedule, such as on a periodic basis. The external system transmits the SPC frame to the implantable medical device. In response, the implantable medical device transmits the SPC response frame to the external system and adjusts its timers such that the timers in the external system and the implantable medical device operate in synchronization.

It is to be understood that the above detailed description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method for data transmission between an implantable medical device and an external system, the method comprising:
   producing channel selection commands each specifying a channel in a scan channel list when a scan timer escape interval expires, the scan channel list including channels selected from a plurality of channels each representing a predetermined frequency band;
   performing a channel hopping in response to each of the channel selection commands, the channel hopping making the channel specified in the each of the channel selection commands an active channel;
   performing data transmission between the implantable medical device and the external system using the active channel during a synchronous scan mode during which the channel hopping in the external system and the channel hopping in the implantable medical device are controlled to be synchronous;
   starting an asynchronous scan mode in response to interruption of the data transmission resulting from making a predetermined number of attempts to transmit data using different channels in the scan channel list without success; and
   restoring the synchronization of the channel hopping in the external system and the channel hopping in the implantable medical device during the asynchronous scan mode.

2. The method of claim 1, wherein producing the channel selection commands comprises producing each of the channel selection commands when a synchronous scan timer escape interval expires during the synchronous scan mode, the channel selection commands each specifying a channel in a synchronous scan channel list of the scan channel list.

3. The method of claim 2, wherein starting the asynchronous scan mode comprises:
   counting a synchronous scan hop count during the synchronous scan mode;
   starting the asynchronous scan mode when the synchronous scan hop count reaches a predetermined maximum hop count;

incrementing the synchronous scan hop count when the synchronous scan timer escape interval expires; and resetting the synchronous scan hop count in response to a signal indicative of successful data transmission.

4. The method of claim 3, wherein producing the channel selection commands comprises producing each of the channel selection commands when an asynchronous scan timer escape interval expires during the asynchronous scan mode, the channel selection commands each specifying a channel in an asynchronous scan channel list of the scan channel list.

5. The method of claim 4, further comprising:

generating the synchronous scan channel list including a first array of channels listed as a synchronous hopping sequence, the first array of channels selected from the plurality of channels; and generating the asynchronous scan channel list including a second array of channels listed as an asynchronous hopping sequence, the second array of channels selected from the plurality of channels, wherein the second array of channels is a subset of the first array of channels.

6. The method of claim 5, wherein the asynchronous scan timer escape interval has a length allowing the external system to hop through all channels of its asynchronous scan channel list while the implantable medical device stays with one channel of its asynchronous scan channel list.

7. The system of claim 5, wherein generating the synchronous scan channel list comprises generating the first array of channels to include all channels of the plurality of channels.

8. The system of claim 5, wherein generating the synchronous scan channel list comprises generating the first array of channels to include preferred channels selected from the plurality of channels.

9. The method of claim 1, further comprising transmitting commands selected from the channel selection commands from the external system to the implantable medical device according to a predetermined synchronization-maintenance schedule.

10. The method of claim 9, further comprising transmitting information specifying the scan channel list from the external system to the implantable medical device.

11. The method of claim 1, wherein restoring the synchronization of the channel hopping in the external system and the channel hopping in the implantable medical device comprises:

transmitting a scan command from the external system to the implantable medical device;

receiving a response signal to the scan command transmitted from the implantable medical device to the external system; and resynchronizing the channel hopping in the external system and the channel hopping in the implantable medical device when the response to the scan command is received, the response to the scan command indicating a match between the active channels of the external system and the implantable medical device.

12. The method of claim 1, wherein specifying a channel in a scan channel list includes specifying a channel in a scan channel that includes a plurality of channels distributed over a frequency range between approximately 402.0 MHz and 405.0 MHz.

13. The method of claim 1, wherein specifying a channel in a scan channel list includes specifying a channel in a scan channel that includes a plurality of channels distributed over a frequency range between approximately 863.0 MHz and 870.0 MHz.

14. The method of claim 1, wherein specifying a channel in a scan channel list includes specifying a channel in a scan channel that includes a plurality of channels distributed over a frequency range between approximately 902.25 MHz and 927.75 MHz.

* * * * *